United States Patent [19]

Tillay

[11] Patent Number: 4,666,445
[45] Date of Patent: May 19, 1987

[54] INTRAOCULAR LENS WITH SHAPE MEMORY ALLOY HAPTIC/OPTIC AND METHOD OF USE

[76] Inventor: Michael J. Tillay, 244 N. Olive, Unit E, Orange, Calif. 92666

[21] Appl. No.: 782,751

[22] Filed: Oct. 1, 1985

[51] Int. Cl.⁴ .............................................. A61F 2/16
[52] U.S. Cl. ........................................ 623/6; 623/66; 128/1 R
[58] Field of Search ...................... 623/6, 66; 128/1 R

[56] References Cited

U.S. PATENT DOCUMENTS

| | | |
|---|---|---|
| 3,620,212 | 11/1971 | Fannon et al. |
| 3,786,806 | 1/1974 | Johnson et al. |
| 3,890,977 | 6/1975 | Wilson |
| 4,426,741 | 1/1984 | Bittner |
| 4,446,582 | 5/1984 | Hanna ..................................... 623/6 |
| 4,466,705 | 8/1984 | Michelson |
| 4,527,294 | 7/1985 | Heslin |
| 4,573,998 | 3/1986 | Mazzocco ............................. 623/6 |

FOREIGN PATENT DOCUMENTS

0145166 12/1984 European Pat. Off.

Primary Examiner—Richard J. Apley
Assistant Examiner—Alan W. Cannon
Attorney, Agent, or Firm—Burns, Doane, Swecker & Mathis

[57] ABSTRACT

An intraocular lens having a lens body, at least one flexible haptic and a component of shape memory alloy operatively connected to the haptic to change the overall dimensions of the lens for implantation of the lens is disclosed. An intraocular lens having a lens body and a component of shape memory alloy operatively connected to the body to change the overall dimensions of the lens is also disclosed.

21 Claims, 16 Drawing Figures

FIG_1

FIG_3

FIG_2

FIG_4

FIG_5

FIG_6

FIG_7

FIG_8

FIG_9

FIG_10

FIG_11

FIG_12

FIG_13

FIG_15

FIG_14

FIG_16

INTRAOCULAR LENS WITH SHAPE MEMORY ALLOY HAPTIC/OPTIC AND METHOD OF USE

BACKGROUND OF THE INVENTION

The present invention relates to intraocular lenses and more particularly to improved haptics and optics for intraocular lenses.

Intraocular lenses are employed as replacements for the crystalline lens after either extracapsular or intracapsular surgery for the removal of a cataract. Intraocular lenses are generally of two types, those that are placed in the anterior chamber, i.e., between the iris and the cornea, and those that are placed in the posterior chamber, i.e., behind the iris. Both types of lenses are conventionally employed with the choice between an anterior chamber and a posterior chamber lens being partly dictated by requirements of the patient and partly dictated by the preferences of the physician inserting the lens. A third type of lens, known as iris-fixated lenses because they are secured to the iris periphery, can be thought of as being within one of the two types above, in that their optic portion is in either the anterior or posterior chamber.

Intraocular lenses normally consist of an optic with at least one and preferably two or more haptics that extend generally radially from the optic and contain distal portions that normally seat in the scleral spur for an anterior chamber lens and either in the ciliary sulcus or within the lens capsule for a posterior chamber lens. The optic normally comprises a circular transparent optical lens. The haptic in most lenses is a flexible fiber or filament having a proximate end affixed to the lens and having a distal end extending radially away from the periphery of the lens to form a seating foot. Several haptic designs are currently in use, for example, a pair of C-shaped loops in which both ends of each loop are connected to the lens, and, for example, J-shaped loops in which only one end of the loop is affixed to the lens.

The optimum position for a posterior chamber lens is in the capsular bag. This is an extremely difficult maneuver for the surgeon to accomplish. When a posterior chamber lens is employed it must be placed through the small pupillary opening, and the final haptic position is hidden behind the iris and not visible to the surgeon. It is therefore highly desirable to keep the overall dimensions of the posterior chamber lens as small as possible during implantation, letting it expand when it is finally situated where the surgeon intends, usually in the capsular bag. A small device is easier to manipulate in the eye, reduces the chance of the haptics coming in contact with the corneal endothelial tissue, and allows the surgeon ease of insertion, as he must often insert a lens with a 14 mm overall dimension through a pupil of 5 to 8 mm diameter. A smaller lens also reduces the lens/iris contact and can better guarantee that the intraocular lens and its haptics will be in the capsular bag. U.S. Pat. No. 4,527,294, discloses a lens having haptics that are capable of being compressed toward the lens body and detachably held thereon. This, however, would require a complicated maneuver for the surgeon and a two-handed insertion technique. Other proposals have sought to attach the distal end of the haptic to the periphery of the optic; this attachment would then be released mechanically by the surgeon after implantation. Unfortunately, the surgeon would have the problem of the uncertainty of finding and releasing the mechanism when the lens periphery is hidden behind the iris after implantation. It would therefore be desirable to have a posterior chamber intraocular lens in which haptics would remain closed until placed behind the iris and would then open automatically without further instrument intervention. This could guarantee successful capsular bag implantation.

As mentioned earlier, intraocular lenses are characterized by a lens body and a plurality of flexible haptics which are usually radially resilient and that extend outwardly from the periphery of the lens and which gently, but elastically, engage appropriate circumferential eye structure adjacent the iris or within the capsular bag. This resiliency is due to the elastic properties of the materials of the haptic. The result is a haptic which when compressed and released will uncontrollably spring back immediately. This property makes the process of implantation and final positioning of the lens difficult since the haptics must be constrained during implantation. U.S. Pat. No. 4,527,294 discloses haptics having a manipulator attached thereto to control the springback until the elns is in final position. U.S. Pat. No. 4,426,741 discloses a closed-loop haptic having a pivotal haptic/optic connection to mitigate the uncontrollable springback of the haptic material. It would be very desirable to have a lens having a mechanical memory whereby the device could be deformed from its free shape to a compact shape which it would maintain for easy implantation and that would restore itself to its free shape in situ without the complex manipulations required in U.S. Pat. No. 4,527,294 mentioned earlier.

Also, once situated, the flexibility of the conventional haptic material makes the lens susceptible to decentration from being pushed by vitreous pressure from behind the lens or shifting due to pressure from adjacent ocular tissue. It would be desirable for centration purposes to have a lens which is flexible where it contacts ocular tissue and which is relatively rigid at the haptic/optic junction.

In recent years intraocular lenses with and without haptics having relatively soft body portions have been provided such that the body portion could be folded generally across the diameter thereof for insertion into a smaller opening during implantation of the lens. U.S. Pat. No. 4,466,705 to Michelson, which is incorporated herein by reference, discloses a fluid sheath having liquid therein. The use of a liquid or hydrogel allows the lens body to be folded before insertion and then subsequently filled when in position. Unfortunately, the soft materials used for the bodies of these lenses lack the restorative strength sometimes required to return to their original shape. It would be highly desirable to have a lens of such soft material not necessarily having haptics but having a component having a mechanical memory associated with the lens body that would restore the soft lens to its original shape and would also provide dimensional stability to the lens in its final position in the eye.

In the past shape memory alloys have been proposed for use in the medical field. For example, U.S. Pat. No. 3,620,212 proposes the use of such an alloy in an intrauterine contraceptive device, U.S. Pat. No. 3,786,806 proposes the use of such alloy in a bone plate, and U.S. Pat. No. 3,890,977 proposes the use of such an alloy to bend a catheter or cannula. The foregoing patents rely on the temperature-transition property of shape memory alloy. In addition, European Patent Application No. 0 145 166, published June 19, 1985, discloses the use of shape memory alloys exhibiting pseudoelasticity and which display stress-induced martensite in the above medical devices. None of those disclosures, however, suggest the use of any shape memory alloy as an integral part of a device to be permanently implanted within the extremely sensitive and close confines of the human eye. Specifically, none of those disclosures contemplate the use of shape memory alloy as an active and precise positioning mechanism. None of those disclosures realize the importance of not only being able to insert an intraocular lens through several minute openings (an incision, pupilary opening and the anterior opening of the capsular bag) during microsurgery, but also to have the lens situate itself in a precise location, and fixate that position with calculable dimensional stability. By comparison, the devices described in the prior art would appear crude and non-analogous. It would therefore be most desirable to have an intraocular lens that would utilize extraordinary properties of shape memory alloy for precise movement and positioning of a lens within the human eye.

SUMMARY OF THE INVENTION

The purpose of the instant invention is to provide an intraocular lens having a guaranteed post-operative shape, greater stability at the haptic-optic connection, the ability to be implanted through a smaller incision, and which is less subject to displacement and shifting from side to side. To accomplish this purpose there is provided an intraocular lens having a lens body, preferably at least one flexible haptic connected to the lens body, and a contouring means of shape memory alloy exhibiting either temperature transition or pseudoelasticity, operatively connected to the body, to the haptic, or to the body and the haptic, to change the overall dimensions of the lens for implantation of the lens.

Specifically, there are provided intraocular lenses including contouring means of shape memory alloy as follows:

traditional lenses, i.e. those having haptics and hard optics, wherein the contouring means is associated with the haptics and the alloy exhibits either temperature transition or pseudoelasticity;

soft body lenses wherein the contouring means is associated with the lens body and the alloy exhibits either temperature transition or pseudoelasticity;

soft body lenses having haptics wherein the contouring means is associated with either temperature transition or pseudoelasticity, and wherein the lens body and the haptics may be made from the same type alloy or different type allays; and soft body lens having haptics wherein the contouring means is integral with a portion of the lens body and the haptics and the alloy exhibits either temperature transition or pseudoelaticity.

Accordingly, a first aspect of the present invention provides an intraocular lens comprising:

a lens body;

at least one flexible haptic having a proximate end and a distal end, said proximate end connected to said lens body; and contouring means of shape memory alloy operatively connected to said haptic to change the overall dimensions of the lens for implantation of the lens.

A second aspect of the invention provides an intraocular lens comprising:

a lens body;

at least one flexible haptic having a proximate end and a distal end, said proximate end connected to said lens body; and contouring means of shape memory alloy having a martensitic state and an austenitic state, said means operatively connected to said haptic, said means capable of being deformed dimensionally while in the martensitic state, a change from said martensitic state to said austenitic state recovering said means to its non-deformed dimension to cause movement of said haptic with respect to said body.

A third aspect of the present invention provides an intraocular lens comprising:

a lens body;

at least one flexible haptic connected to said lens body; and contouring means of shape memory alloy which is pseudoelastic displaying reversible, stress-induced martensite at body temperature, said means operatively connected to said haptic to cause movement of said haptic with respect to said body.

A fourth aspect of the present invention provides an intraocular lens comprising:

a lens body of generally soft material; and contouring means of shape memory alloy operatively connected to said lens body to change the overall dimensions of the lens for implantation of the lens.

A fifth aspect of the present invention provides an intraocular lens comprising:

a lens body of generally soft material;

at least one flexible haptic connected to said lens body; and contouring means of shape memory alloy integral with a portion of said body and said haptic to change the overall dimensions of said lens.

A sixth aspect of the present invention provides a method of installing an intraocular lens comprising the steps of:

providing an intraocular lens having a lens body of generally soft material and a contouring means of shape memory alloy, said means capable of recoverable deformation, said means being operatively connected to said body to change the overall dimensions of the lens;

deforming said lens to a smaller overall dimension;

positioning said lens in the body; and recovering said means to a larger overall dimension.

DESCRIPTION OF THE PREFERRED EMBODIMENTS

Various aspects of the present invention will evolve from the following detailed description of the preferred embodiments thereof, which should be taken in conjunction with the heretofore-described drawing.

Figure 1:
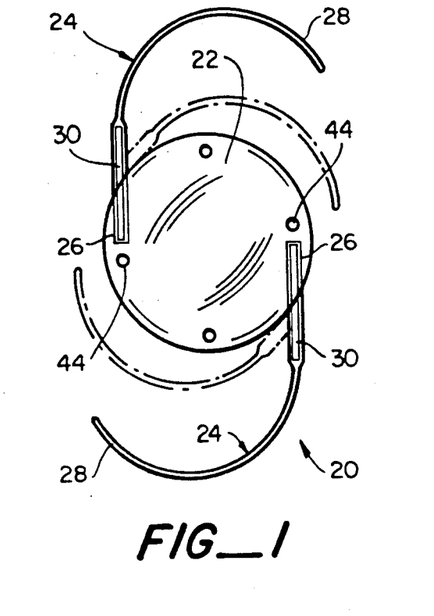
FIG. 1 is a front view of an embodiment of the present invention.

With reference to the drawing, FIG. 1 illustrates the intraocular lens of the instant invention shown generally at 20, having a lens body 22 and flexible haptics 24 mounted thereto. Each haptic 24 has a proximate end 26 and a distal end 28. The proximate ends 26 are connected to the lens body 22. The lens further includes contouring means 30 of shape memory alloy operatively connected to the haptics 24 to change the overall dimensions of the lens 20 for implantation of the lens 20. In this embodiment, the contouring means 30 is associated with a portion of the haptic 24 generally at the proximate end 26 of the haptic, and is capable of moving the haptic as the contouring means changes shape. Specifically, the contouring means 30 of shape memory alloy is integral with a portion of the haptic at the proximate end 26.

Materials, both organic and metallic, possessing shape memory, are well known. An article made from such materials can be deformed from an original, heat-stable configuration to a second, heat-unstable configuration. The article is said to have shape memory (mechanical memory) for the reason that, upon the application of heat alone, it can be caused to revert, or to attempt to revert, from its heat-unstable configuration to its original, heat-stable configuration, i.e., it "remembers" its original shape. Alloys of this type are herein defined as exhibiting "temperature transition".

Among metallic alloys, the ability to display shape memory is a result of the fact that the alloy undergoes a reversible transformation from an austenitic state to a martensitic state with a change in temperature. This transformation is sometimes referred to as a thermoelastic martensitic transformation. An article made from such an alloy is easily deformed from its original configuration to a new configuration when cooled to a temperature below which the alloy is transformed from the austenitic state to the martensitic state.

The temperature at which this transformation begins is usually referred to as $M_s$ and the temperature at which it finishes is $M_f$. When an article thus deformed is warmed to a temperature at which the alloy starts to revert back to austenite, referred to as $A_s$ ($A_f$ being the temperature at which the transformation is complete), the deformed object will begin to return to its original configuration. Also, the alloy is considerably stronger in its austenitic state than in its martensitic state.

One alloy of the type that may be used to fabricate a contouring means 30 is the subject of U.S. Pat. No. 3,351,463, which is incorporated herein by reference. Other literature desribing the processing and characteristics of suitable compositions includes an article by Dr. William J. Buehler, the principal developer of the material, and William B. Cross, entitled "55 Nitinol - Unique Alloy Wire," which appeared in the June 1969 issue of *Wire Journal.* A description of the materials and certain of the properties also may be found in the brochure entitled "Nitinol Characterization Studies" dated September 1969. This document, identified as N-69-36367, or NASA CR-1433, is available from the Clearinghouse for Scientific and Technical Information, Springfield, VA 22151. All of these publications are incorporated herein by reference.

Examples of shape memory alloys exhibiting temperature transition are disclosed in U.S. Pat. Nos. 3,174,851 and 3,672,879, incorporated herein by reference. A titanium-nickel-cobalt alloy is disclosed in U.S. Pat. No. 3,558,369. Suitable binary nickel-titanium shape memory alloys are well known to those skilled in the art and, for example, are described in the patents and article of Buehler et al mentioned above. These binary shape memory alloys are commercially available from a number of suppliers, one of which is Raychem Corporation in Menlo Park, Calif.

The preferred shape memory alloys for the fabrication of a contouring means are the nickel-titanium-vanadium alloys disclosed in U.S. Pat. No. 4,505,767 issued Mar. 19, 1985, the disclosure of which is incorporated herein by reference. A most preferred alloy is "Alloy T", commercially available from Raychem Corporation and having the composition 48.5 nickel, 45.5 titanium and 6.0 vanadium, in atomic percent.

In contrast to shape memory alloys exhibiting temperature transition, many shape memory alloys are known to be "pseudoelastic," displaying reversible stress-induced martensite. When a shape memory alloy sample exhibiting stress-induced martensite is stressed at a temperature above $M_s$ (so that the austenitic state is initially stable), but below $M_d$ (the maximum temperature at which martensite formation can occur even under stress) it first deforms elastically and then, at a critical stress, begins to transform by the formation of stress-induced martensite. Depending on whether the temperature is above or below $A_s$, the behavior when the deforming stress is released differs. If the temperature is below $A_s$, the stress-induced martensite is stable; but if the temperature is above $A_s$, the martensite is unstable and transforms back to austenite, with the sample returning (or attempting to return) to its original shape. The effect is seen in almost all alloys which exhibit a thermoelastic martensitic transformation, along with the shape memory effect. However, the extent of the temperature range over which stress-induced martensite is seen and the stress and strain ranges for the effect may vary greatly with the alloy. A complete discussion of the pseudoelastic alloY is given in European Patent Application No. 0-145-166, mentioned earlier, the disclosure of which is incorporated herein by reference. The above-mentioned U.S. Pat. No. 4,505,767 also discloses a nickel/titanium/vanadium alloy having stress-induced martensite over a wide temperature range suitable for the fabrication of the "pseudoelastic" alloy embodiments of contouring means 30.

In summary, it is within the scope of the invention to fabricate the contouring means of the various embodiments from shape memory alloys which exhibit temperature transition or from alloys which exhibit pseudoelasticity. The following description will generally refer to the temperature transition type alloy for ease of explanation.

With reference to the drawing, in the embodiment of FIG. 1, when the contouring means 30 of shape memory alloy exhibiting temperature transition is cooled to its martensitic state and is subsequently deformed, it will retain its new, deformed shape, but, when it is warmed to its austenitic state, the original, final shape will be recovered.

Figure 2:
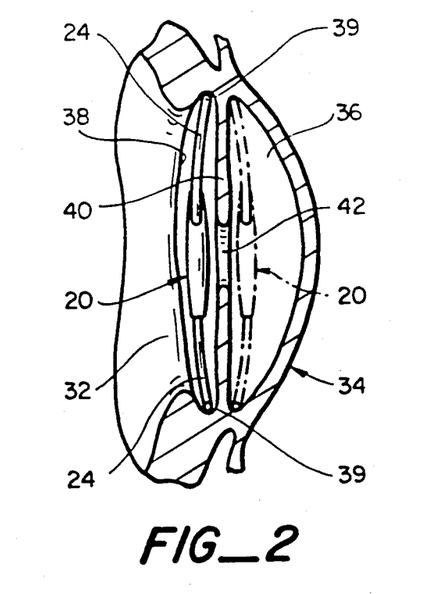
FIG. 2 is a sectional view showing the lens of FIG. 1 within the capsular bag of the posterior chamber of an eye. The Figure also illustrates the placement of such a lens shown in phantom within the anterior chamber.

FIG. 2 illustrates the intraocular lens 20 of FIG. 1 placed in the capsular bag of the posterior chamber 32 of eye noted generally at 34. A lens may also be placed in the anterior chamber 36 as shown in phantom. It can be seen that the haptics 24 extend to and contact the capsular bag 38. It is within the scope of the invention to have the haptics extend to and contact the ciliary sulcus 39. It should be noted that the haptics 24 should be vaulted or angled away from the portion of the iris 40 adjacent the pupil 42.

Figure 3:
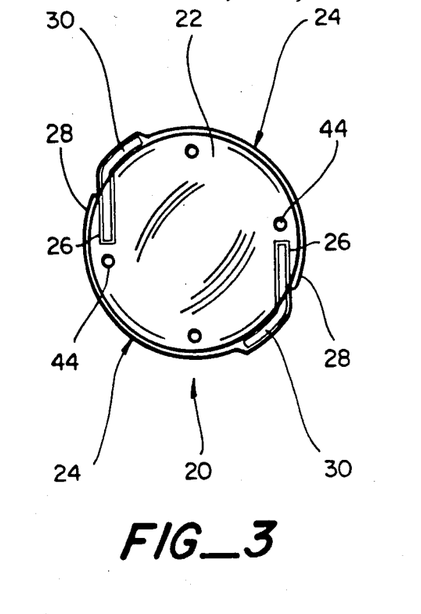
FIG. 3 is a front view corresponding to FIG. 1 wherein the haptics have been compressed.

It is understood that in this embodiment the contouring means 30 is preferably made from a shape memory alloy that has a transition temperature range, i.e., exhibiting temperature transition, and the contouring means 30 has been formed into a final shape as shown in FIG. 1 and has been subsequently deformed to a deformed shape as can now be seen in FIG. 3 at a temperature below said range, the overall dimensions of lens 20 being altered in correspondence to said shapes. As mentioned earlier in this embodiment, the contouring means 30 is associated with the portion of the haptic 24 at the proximate end 26 of the haptic. As seen in FIG. 1, the final shape of the contouring means 30 is in this embodiment generally straight and as seen in FIG. 3 the deformed shape of the contour means is bent to be complementary with the periphery of the lens 22. It can be seen in both FIGS. 1 and 3 that the remaining portion of the haptic 24 is curved and is generally complementary to the periphery of the lens 22. It should be remembered that the contouring means may in an alternate embodiment be made from a shape memory alloy known to display stress-induced martensite although the shape memory alloy and would require separate mechanical restraint during installation. The difference in the operation of such a device will be appreciated after reading the description of the embodiment illustrated in FIGS. 13–16.

Figure 4:
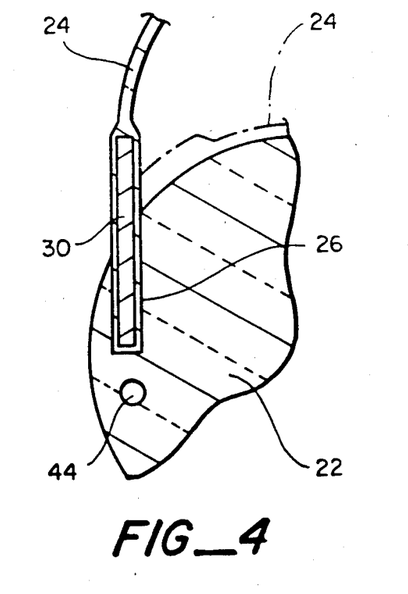
FIG. 4 is an enlarged, partial sectional view of a portion of FIG. 1 showing the connection of a haptic to the lens body.

FIG. 4 is an enlarged view of a portion of FIG. 1 illustrating the interconnection of the contouring means 30, haptic 24 and lens body 22. In this embodiment, the contouring means 30 is integral with the haptic 24 at the proximate end 26 of the haptic. The contouring means is actually encapsulated in the material from which the haptic 24 is formed. Typical materials are polymethylmethacrylate (PMMA), prolene, polypropylene, nylon, silicone or other material suitable for implantation within the body. The lens body may also be made of PMMA, especially PMMA with an ultraviolet absorber, silicone, hydrogel, glass, or other well-known suitable materials that may vary from the hard qualities of PMMA to the soft qualities of silicone or hydrogel. In general, it is preferable to encapsulate the contouring means of this embodiment and those yet to be described to protect and insulate them.

The contouring means 30, as shown in FIG. 4, each act as an integral metallic strut encapsulated within the loop-like haptic 24. The stiffness of the haptics which effects the stability and rigidity at the haptic-optic connection is determined by the length and thickness as well as the mechanical properties of the alloy.

It should be understood that the shape memory alloy can facilitate the motion necessary to seat the haptics without causing a long-term pressure problem, i.e., a haptic of the instant invention can position itself and exert carefully controlled in situ pressure. In contrast, a conventional haptic must have enough strength to move itself outward which means that it will, in many placements, have excess residual strength that can create a long-term pressure problem.

As mentioned above, the contouring means and thus the haptic 24 are deformed prior to implantation by a surgeon enabling the surgeon to implant the lens by slipping the lens body with the haptics, in essence, clinging to it, into the capsular bag. This unique lens enables the surgeon to guarantee that the loops would be in the bag and to eliminate the problem of managing wide loops discussed earlier with respect to prior art devices. With the lens then firmly in the capsular bag, the surgeon could rotate the optic easily, such as by insertion of an instrument in holes 44 in lens body 22 without worrying about the haptics. The contouring means opens up to its final shape and the haptics fixate themselves in the capsular bag as the body warms the shape memory alloy to the body temperature. To guarantee that the lens is fixed in position, the surgeon could retract the iris at the haptic position to see if the contouring means was generally straight, thus guaranteeing that transition has occurred.

Figure 5:
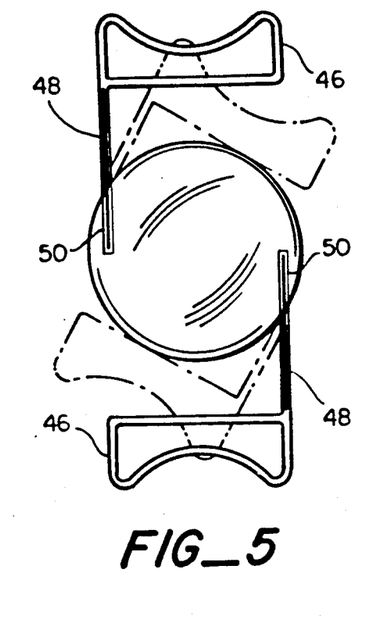
FIG. 5 is a view similar to FIG. 1 of another embodiment having a loop-shaped haptic. The deformed position of the haptic is shown in phantom.

FIG. 5 illustrates an alternative embodiment having a loop-shaped flexible haptic. In this embodiment the haptic 46 encapsulates a strut-like contouring means 48 which is associated with a portion of the haptic generally at the proximate end 50 of the haptic. The contouring means is shown to be straight in final shape but when it is deformed to a deformed shape, i.e., bent, the overall dimensions of the lens are altered.

Figure 6:
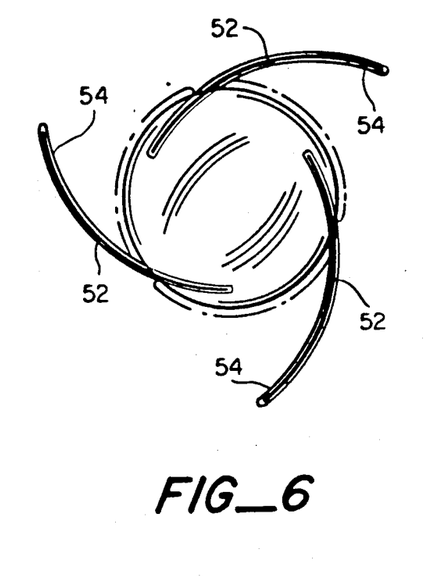
FIG. 6 is a view similar to FIG. 1 of yet another embodiment having more than two haptics having integral contouring means the entire length thereof. The position of the deformed haptics is shown in phantom.

FIG. 6 shows yet another alternate embodiment wherein the contouring means 52 is integral with the entire haptic 54. In this embodiment, the contouring means is encapsulated with suitable material over the entire length of the contouring means. The use of a longer contouring means of shape memory alloy allows for a smaller diameter shape memory alloy component since the entire length of the haptic can be deformed and contoured. This Figure also illustrates the use of more than two haptics 54.

Figure 7:
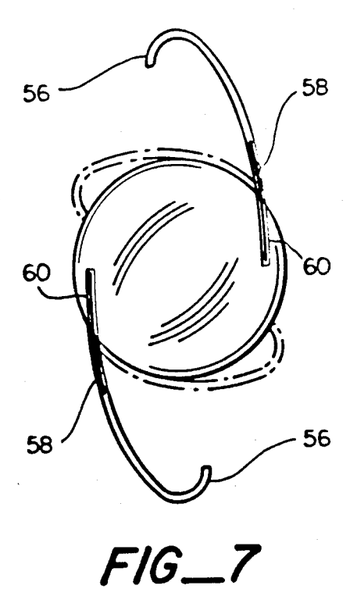
FIG. 7 is a view similar to FIG. 1 of still another embodiment having modified J-loop haptics. The position of the deformed haptics is shown in phantom.

FIG. 7 shows yet another embodiment of the instant invention wherein haptic 56 is a Sinskey-modified J-loop having a contouring means 58 associated with a portion of the haptic 56 generally at the proximate end 60 of the haptic. The retracted haptic having a deformed contouring means 58 is shown in phantom.

Figure 8:
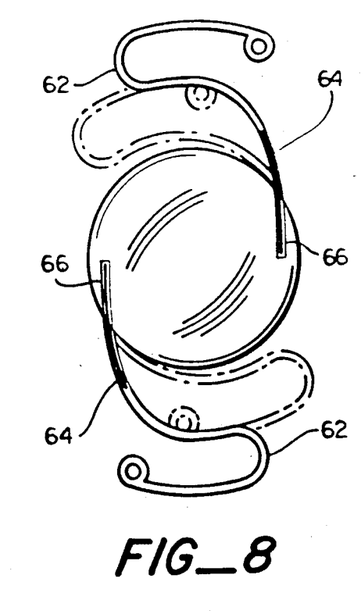
FIG. 8 is a view similar to FIG. 1 of yet another embodiment having an open-loop haptic. The position of the deformed haptic is shown in phantom.

FIG. 8 shows yet another embodiment of the instant invention wherein haptic 62 is in contact with contouring means 64, which is associated with a portion of the haptic 62, generally at the proximate end 66 of the haptic. The position of the haptic corresponding to a deformed contouring means 64 is also shown in phantom. In this embodiment the contouring means pushes the haptic 62 away from the periphery of the lens body.

Figure 9:
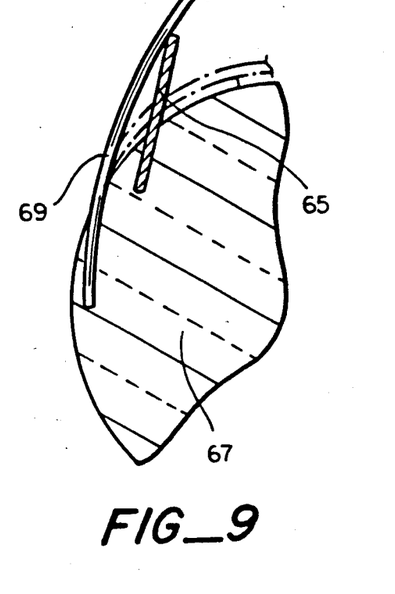
FIG. 9 is a view similar to FIG. 4 of the mounting of a haptic and strut-like contouring means.

FIG. 9 is a view similar to FIG. 4 of the operative connection of a strut-like contouring means 65 to the body 67 and a haptic 69. The haptic 69 is a conventional haptic of conventional haptic material and having a desired overall configuration. The contouring means is separated connected to the body 67 and connects with the haptic at some point along the length thereof remote from the haptic proximate end. The position of the haptic corresponding to a deformed contouring means 65 is shown in phantom. It is understood that this type of contouring means may be applied to the previously discussed embodiments of FIGS. 1-5, 7 and 8.

Figure 10:
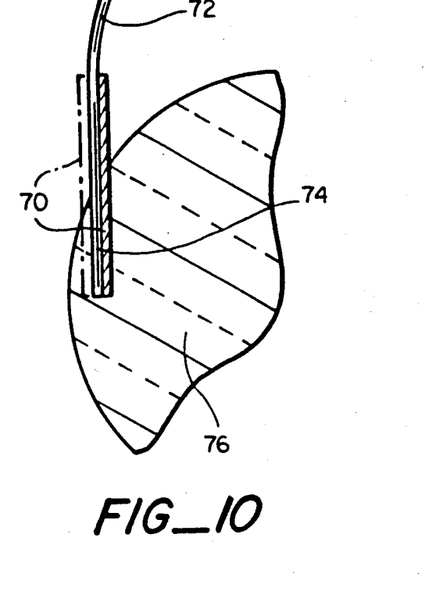
FIG. 10 is a view similar to FIG. 4 of the mounting of a haptic and a separate contouring means mounted in the lens body.

FIG. 10 is a view similar to FIG. 9 wherein the contouring means 70 is associated with a portion of the haptic 72 generally at the proximate end 74 of the haptic. In this embodiment the contouring means need not be integral with the body of the haptic 72 but is merely in contact with haptic 72. The contouring means 70, as mentioned earlier, may be coated with suitable material that is body-compatible, but may constitute a separate element. It can be understood that this type of contouring means 70 may be applied to the previously discussed embodiments of FIGS. 1-5, 7 and 8. In the embodiment of FIG. 10, the contouring means 70 has straightened to its final shape to push the haptic 72 outward such that the distal end of the haptic 72 is moved away from the periphery of the lens body 76. It is within the scope of the invention to have the contouring means 70 mounted outside (as shown in phantom) to the left of haptic 72 such that when bent to a deformed shape it would push the haptic 72 into closer proximity to the periphery of the lens body 76. Upon transition from a martensitic state to an austenitic state the contouring means 70 would straighten allowing the haptic 72 to straighten (due to its own structural integrity) such that the distal end of the haptic 72 would move away from the periphery of the lens body 76.

Figure 11:
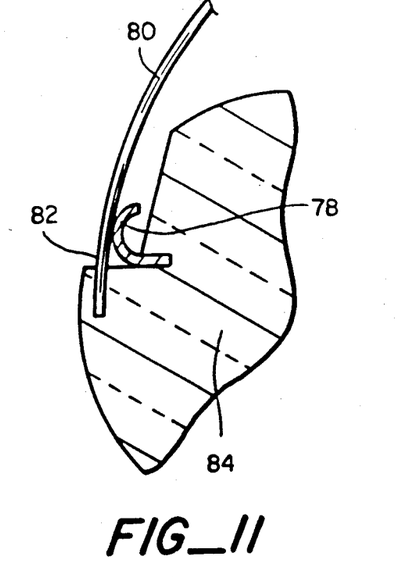
FIG. 11 is view similar to FIG. 4 showing the mounting of an alternate embodiment having separate contouring means and haptic.

FIG. 11 is a view similar to FIG. 9 of still another embodiment wherein the contouring means 78 is a generally C-shaped (bent) piece of shape memory alloy which is associated with a portion of the haptic 80 generally at the proximate end 82 is in operative contact with the body and the haptic and is capable of moving the haptic as the contouring means changes in shape. In this embodiment a conventional haptic of whatever distal configuration is embedded in the lens body 84 to naturally conform to the periphery of the body. The contouring means 78 in its deformed shape would be primarily straight except for a portion of the contouring means which would be embedded in the lens body 84 to anchor the contouring means 78. Upon recovery the contouring means 78 would become generally C-shaped (bent) pushing against the haptic 80 and moving the haptic 80 away from the lens body 84.

Figure 12:
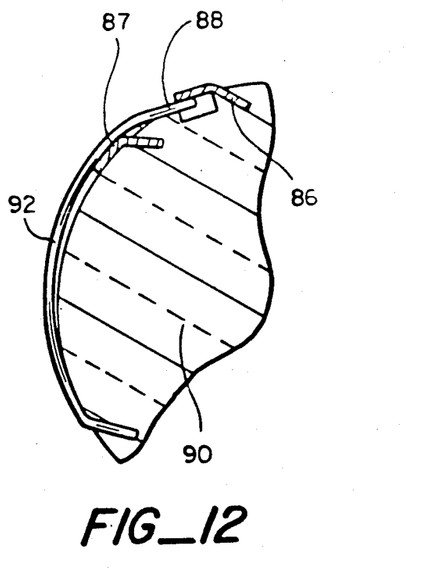
FIG. 12 is a view similar to FIG. 4 of yet another alternate embodiment wherein the contouring means is used to secure the free or distal end of the haptic with respect to the lens body.

FIG. 12 is a view similar to FIG. 9 of yet another embodiment wherein the contouring means 86 is also positioned between and in contact with said body and said haptic. It is understood that the contouring means of the embodiments of FIGS. 9, 10, 11 and 12 are positioned between and in contact with the body and the haptic. In the embodiment of FIG. 12 the distal end 88 of the haptic normally extends away from the periphery of the lens body 90 and the contouring means 86 is capable of retaining and then releasing the distal end 88 of the haptic 92 as the contouring means 86 changes shape. It is also within the scope of the invention to have a contouring means 87 (shown in phantom) similar to contouring means 86 which is mounted with respect to the lens body 90 to push against the underside of the distal end 88 of the haptic 92 upon return to final shape to force the distal end 88 of the haptic 92 away from a temporarily secured position on or near the periphery of lens body 90. The distal end 88 could, for example, be forcefit into a notch in lens body 90 and contouring means 87 would be positioned below the notch to force the distal end away from the notch. Other securing means such as biocompatible adhesive material, etc., would be within the scope of the invention.

Figure 13:
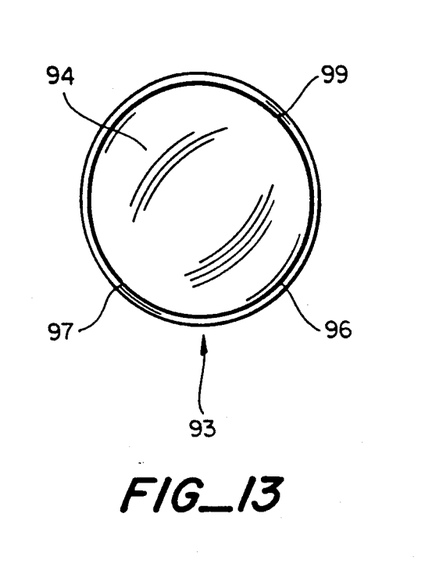
FIG. 13 is a front view of a soft lens embodiment of the instant invention.
Figure 16:
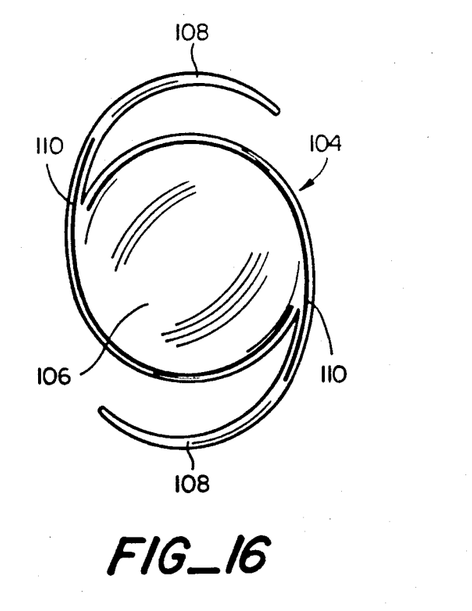
FIG. 16 is a front view of another embodiment of a soft lens with haptics and having a combination body and haptic contouring means.

FIG. 13 illustrates a soft lens embodiment of the instant invention shown generally at 93. In this embodiment the lens body 94 is especially made from soft material such as silicone or any other material which has very little structural integrity. The lens body 94 may be one piece or it may comprise a sheath which may be filled with liquid or gel. Previously cited U.S. Pat. No. 4,466,705, discloses numerous other materials useful in the fabrication of a soft-liquid filled lens. As mentioned earlier, it is advantageous to have a soft lens which may be folded across the diameter of the lens body 94 for surgical insertion into a smaller opening. But, due to the lack of structural integrity of the material which comprises the soft body the inserted lens is often difficult or impossible to unfold in situ. The lack of structural integrity of a soft material is also a problem from a stability standpoint as with age the capsular bag is believed to shrink and exert pressure on the lens. In this embodiment a contouring means 96 preferably in the form of a closed-loop frame is encapsulated within the perimeter of the lens body 94. It is understood that the "frame" may be discontinuous, for example at points 97 and 99, and may thus comprise one or more discrete elements that will unfold the lens 93. FIG. 16 illustrates a contouring means in the form of a discontinuous frame in a combination body and haptic contouring means as will be further discussed later.

It is also understood that the contouring means will not only positively unfold the soft body lens but will also provide in situ support and stability to prevent the lens from being decentered by movement in the capsular bag and keep the optic from wrinkling, bending or bowing due to pressure from adjacent tissue, etc.

Figure 14:
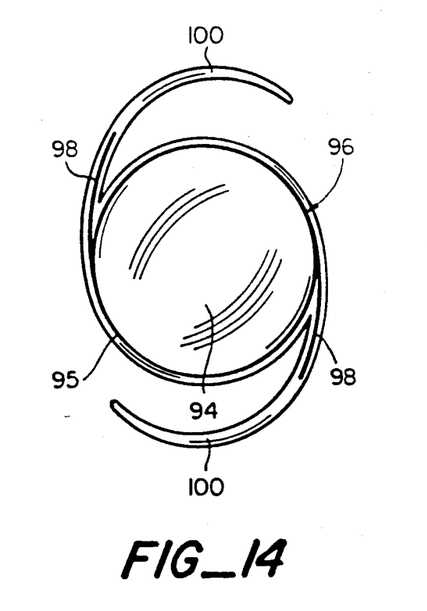
FIG. 14 is a front view similar to FIG. 13 of the soft lens embodiment including the optional haptics which have been deformed to a position near the periphery of the lens.

In FIG. 14, the contouring means noted generally at 96 may optionally have strut-like portions 98 integral with or in contact with the optional haptics 100 of desired configuration which may extend from the frame 95 of the contouring means 96 to move the haptics 100. The strut-like portions 98 may be separate from the closed-loop frame. In such a construction the contouring means comprises separate portions, one associated with the lens body and the other(s) associated with the haptics. It can be appreciated that the alloys used in these portions may be of different type as discussed earlier. In the case of temperature transition alloys the portions may have different recovery times. For example, it would be desirable to have the lens body 94 unfold before the haptics 100 extend from the lens body. This could be accomplished by varying the alloy, conditioning, insulative coating and numerous other expedients kown to those skilled in the art.

The contouring means in FIG. 14 may be made from a temperature transition type of shape memory alloy producing a contouring means which can be deformed at a low temperature prior to insertion and which will upon warming open by itself after insertion. For the same alloy the timing of the portions of the contouring means can be controlled by insulating the portions differently. The contouring means can alternatively be made from a pseudoelastic type shape memory alloy producing a contouring means which can be deformed at room temperature, can be kept deformed by a tool such as a forcep, and will open in situ when released.

As mentioned, it is within the scope of the invention to fabricate the frame 95 of the contouring means 96 including the optional struts 98 from the shape memory alloy described earlier as having a transition-temperature range (temperature transition), i.e., having a martensitic state and an austenitic state the lens recovering upon warming or to fabricate the frame 95 and the optional struts 98 from a shape memory alloy which is pseudoelastic displaying isothermal reversible, stress-induced martensite at body temperature. Furthermore, it is also within the scope of the invention to fabricate the frame 95 of the contouring means from such a stress-induced martensite and to have the strut portions 98 fabricated from a transition-temperature alloy or vice versa.

Figure 15:
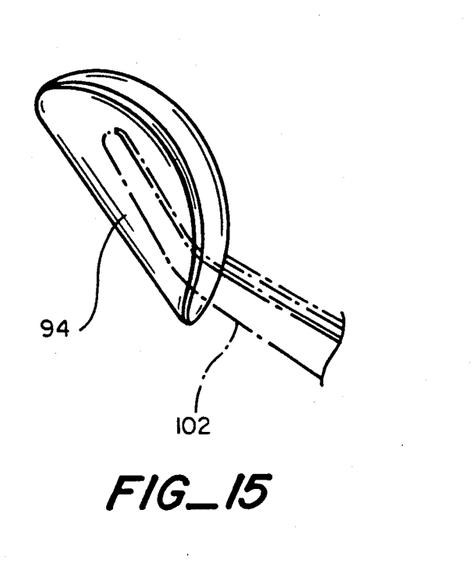
FIG. 15 is a perspective view of the lens shown in FIG. 14 wherein the lens body has been folded across the diameter thereof for implantation. A conventional forcep mechanism is shown in phantom, restraining the lens.

FIG. 14 illustrates an intraocular lens having the optional haptics 100 held or moved in close proximity to the periphery of the lens body 94. FIG. 15 illustrates the lens body 94 further folded. As seen in FIG. 14 the optional contouring means strut portions 98 have been deformed from their final generally straight shape into the curved deformed shape so that the optional haptics 100 are in close proximity to the perimeter of the lens body 94. In FIG. 15, the loop portion of the contouring means is deformed by being folded as the body 94 is folded generally across the diameter thereof. When the contouring means is made from shape memory alloy of the temperature transition type, the various manipulations of the lens, specifically the folding of the lens, including the loop portion of the contouring means and the movement of the struts, if haptics are utilized, may be made when the alloy is cooled at a temperature below which the alloy is transformed from the austenitic state to the martensitic state. This may be done after fabrication of the lens or later by the surgeon. The deformed lens may then be installed and the lens will be warmed by the eye to body temperature, the alloy changing from the martensitic state to the austenitic state, recovering the contouring means to its nondeformed dimension to change the overall dimensions of the lens.

As mentioned earlier, when the contouring means is made from a pseudoelastic alloy, the contouring means is capable of being deformed by the formation of a stress-induced martensite into a deformed shape different from a final shape and is capable of being restrained in a deformed shape such as by the use of a conventional forceps 102, shown in FIG. 15, for insertion into the body. At that point the contouring means is capable of being isothermally transformed from the deformed shape into the final shape.

As shown in FIGS. 13-16, the contouring means is directly connected to the body 94 to allow the body to be folded and restrained generally across the diameter thereof, deforming the contouring means to a deformed state. The means will open the body to its original, final state when unrestrained, such as by removal of the forceps 102. As shown in FIG. 14, the contouring means may also be directly connected to haptic 100 by the strut portions 98 to allow the distal end of the haptic 100 to be moved and restrained adjacent the periphery of the body 94. Said means is also capable of moving the distal ends away from the body 94 in their final state when unrestrained.

FIG. 16 discloses an intraocular lens shown generally at 104 having a lens body 106 of generally soft material and at least one haptic 108 connected to the lens body. The contouring means 110 of shape memory alloy is integral with a portion of the lens body 106 and the haptic 108 to change the overall dimensions of the lens. The contouring means in this embodiment is a discontinuous frame for the lens body 106 as compared to the closed-loop frame shown in FIGS. 13-15. The contouring means 110 is shown to comprise a pair of shape memory elements which are integral with both the lens body 106 and the haptics 108. In this embodiment the shape memory alloy may be either pseudoelastic or temperature transition type shape memory alloy.

As discussed, the present invention also contemplates the method of installing an intraocular lens wherein an intraocular lens having a lens body of generally soft material and a contouring means of shape memory alloy wherein the contouring means is capable of recoverable deformation and is operatively connected to the lens body to change the overall dimensions of the lens. It is understood that in this method the means may be deformed wherein the lens will have a smaller overall dimension. The lens may be positioned within the body and the contouring means recovered to a larger overall dimension. It is also within the scope of the invention to include the step of restraining the contouring means in the deformed condition by the application of a restraining means and subsequent to insertion in the body removing the restraining means after positioning.

All of the foregoing embodiments could be utilized in several ways depending upon type of embodiment, the shape of the embodiment, nature of material of the lens, final placement site, and preferences of the surgeon. There follows a discussion of the possible utilizations and the advantages of each.

The temperature transition type shape memory alloy intraocular lens can be deformed by the manufacturer and packaged in its compressed state, or it may be deformed just prior to implantation by the surgeon at room temperature or thereabout.

The ease-of-implantation advantages of posterior chamber intraocular lens with temperature transition type shape memory alloy associated with the haptics are threefold. First, the lens with its haptics bent toward the lens body has a smaller overall dimension that can be more easily inserted into the eye through the initial incision into the anterior chamber. Second, this small overall dimension allows the surgeon to more easily manipulate the lens in the anterior chamber and slide or drop the lens through the normally small pupillary opening into the posterior chamber behind the iris. Three, since the haptics of the lens would not spring outward from the lens body immediately after releasing it, the whole lens body with its haptics would more easily slide into the capsular bag (or the ciliary sulcus if the surgeon so desired). With the whole lens and its haptics still compressed to the lens body in its final position in the capsular bag, the warming of the shape memory alloy contouring means toward body temperature would be the mechanism for opening the haptics to contact the desired capsular membrane securing it in place. This would eliminate the need for rotating the lens after positioning in the bag because the lens could be inserted with the haptics already rotated to their horizontal or vertical positions as the surgeon chooses. This insertion technique would reduce the chance of ripping or puncturing the capsular bag by one of the haptics during its implantation or its rotation in the capsular bag. Also with added strength of the austenitic state of the shape memory alloy at the haptic/optic junction there will be less chance of decentration in the capsular bag or posterior to anterior displacement due to vitreous pressure from behind the lens. The lens is now firmly seated in the desired place in the capsular bag and this position has been achieved with less contact with and less stress on delicate ocular tissue.

The same advantages are possible when a temperature transition type shape memory alloy is incorporated with the haptic and/or body of a soft body intraocular lens. However, in addition to these, the incorporation would add the following features. With the haptics bent toward the body of the lens the body could be folded or rolled and inserted with a Kelman-McPherson forceps through a smaller incision that is one-half to one-third the length normally used for standard lenses with hard optics. This lens could then be slid down into the pupillary opening directly or allowed to partially unfold and then dropped into the pupillary opening into the posterior chamber and into the capsular bag. The shape memory alloy transition to its austenitic state in the lens body and haptic would then open the folded soft material, securing the lens gently in place. This transition ensures that the lens will unfold to its prefolded condition in the eye that cannot be guaranteed or expected with the soft intraocular lens itself. The austenitic strength of the shape memory alloy would provide the rigidity for the optic and optic-haptic junctures necessary to keep adjacent ocular tissue from refolding, bending, bowing or compromising the lens body or its position in the capsular bag. This tendency to bow or bend is part of the lack of restorative strength of soft material for a soft body intraocular lens. The transition type shape memory alloy incorporated in a soft intraocular lens provides the ease of implantation and foldable advantages of the soft body lens by means of the alloy's deformable characteristics. After implantation and positioning the deformation is recovered as the alloy transforms to its austenitic state and final nondeformed shape. The alloy in the austenitic state also becomes stronger, producing a desirable post-implantation characteristic: rigidity. Shape memory alloy in its austenitic state in the contouring means associated with the lens body and haptic guarantees the shape of the lens body post-operatively and that this shape will not be compromised by pressure from adjacent ocular tissue or vetreous pressure. The desired post-perative shape is guaranteed and position is secure. The deformable nature of the soft material alone could not guarantee this. The shape memory alloy could be incorporated in the contouring means associated with the lens body alone, or the lens body and haptics depending upon the circumference of rigidity that is desired. This circumference could concern itself simply with the integrity of the lens body or by incorporation of the shape memory alloy in the contouring means associated with haptic portions extend the circumference of rigidity by several millimeters to reduce the chances of displacement or decentration of the lens in the posterior chamber.

The temperature transition type shape memory alloy lens could be inserted into the anterior chamber and allowed to transition to its rigid state, or begin its transition in the anterior chamber before rotating or compressing it into the posterior chamber. This transition would also be allowed in the anterior chamber for placement of hard body or soft body anterior chamber lens. The rigidity that the austenitic shape memory alloy would give to soft material would enable an anterior chamber lens to be folded and implanted through a small incision, and hold its shape and position in the anterior chamber without bowing or displacement. This is due to the rigidity in the optic and/or haptic-optic junction. The placement anteriorly would also allow the surgeon to insert the lens without having to rotate it to its final desired position, engaging corneal-scleral and iris tissue along the way. The lens could be inserted with the contouring means deformed and then as the contouring means warm up the lens would secure itself in its final position, engaging only the corneal-scleral tissue that would secure it.

The temperature transition shape memory alloy in soft intraocular lenses has the desirable characteristic of deformability transitioning to rigidity. The pseudoelastic type of shape memory alloy has the rigidity advantages of the temperature transition type soft intraocular lens mentioned above but without its deformability characteristics. The pseudoelastic type in a soft body intraocular lens would assure that it can be folded and when it is released it will return to its prefolded shape. This type of lens with pseudoelastic contouring means could be folded by a standard Kelman-McPherson forceps and inserted through a small incision into the anterior chamber of the eye where it would then unfold upon release of the forceps. If the surgeon so desired the lens could be held in the folded position until it is inserted through the pupillary opening into the posterior chamber and capsular bag. If the lens is allowed to unfold in the anterior chamber it could be implanted much like any other posterior chamber lens by compression or rotation into the posterior chamber or capsular bag. The pseudoelastic type material exhibiting the rigidity of the temperature transition type shape memory alloy at this point would provide stability, preventing the lens body once fixated in position from being wrinkled, bent, or bowed, and its final position from being compromised by pressure from the surrounding tissue.

While the preferred embodiments of the present invention have been described, it should be understood that the various changes, adaptations and modifications may be made therein without departing from the spirit of the invention and the scope of the appended claims.

What is claimed is:

1. An intraocular lens comprising:
a lens body;

at least one flexible haptic having a proximate end and a distal end, said proximate end connected to said lens body; and contouring means of shape memory alloy operatively connected to said haptic to change the overall dimensions of the lens for implantation of the lens wherein the alloy has a transition-temperature range, said contouring means having been formed to a final shape at a temperature above said range and having been deformed to a deformed shape at a temperature below said range, the overall dimensions of the lens being altered in correspondence to said shapes.

2. A lens as in claim 1 wherein said contouring means is in contact with a portion of said haptic generally at the proximate end of said haptic and is capable for moving said haptic as said contouring means changes shape.

3. A lens as in claim 1 wherein said contouring means is integral at said portion of said haptic.

4. A lens as in claim 1 wherein said contouring means is integral with generally the entire haptic and is capable of moving said haptic as said contouring means changes shape.

5. A lens as in claim 1 wherein said contouring means is positioned between and in operative contact with said body and said haptic.

6. A lens as in claim 5 wherein said contouring means is capable of moving said haptic as said contouring means changes shape.

7. A lens as in claim 5 wherein the distal end of said haptic normally extends away from the periphery of said body, said contouring means being in contact with said body and said haptic when in its deformed shape and only to said body when in its final shape, said means being capable of retaining and then releasing said distal end of said haptic as said contouring means changes shape.

8. An intraocular lens comprising:
a lens body;
at least one flexible haptic having a proximate end and a distal end, said proximate end connected to said lens body; and
contouring means of shape memory alloy operatively connected to said haptic to change the overall dimensions of the lens for implantation of the lens wherein the shape memory alloy is pseudoelastic displaying reversible, stress-induced martensite at body temperature and is capable of being deformed by the formation of stress-induced martensite into a deformed shape different from a final shape and is capable of being restrained in the deformed shape for insertion into a body, said means capable of being isothermically transformed from the deformed shape to the final shape.

9. A lens as in claim 8 wherein said means is also directly connected to said body to allow said body to be folded and restrained generally across the diameter thereof deforming said means to a deformed state, said means capable of opening said body to its original final state when unrestrained.

10. An intraocular lens comprising:
a lens body;
at least one flexible haptic connected to said lens body; and
contouring means of shape memory alloy which is pseudoelastic displaying reversible, stress-induced martensite at body temperature, said means operatively connected to said haptic to cause movement of said haptic with respect to said body.

11. An intraocular lens comprising:
a lens body;
at least one flexible haptic having a proximate end and a distal end, said proximate end connected to said lens body; and
contouring means of shape memory alloy having a martensitic state and an austenitic state, said means operatively connected to said haptic, said means capable of being deformed dimensionally while in the martensitic state, a change from said martensitic state to said austenitic state recovering said means to its non-deformed dimension to cause movement of said haptic with respect to said body.

12. A lens as in claim 11 wherein said recovery moves the distal end of said haptic away from the periphery of said body.

13. A lens as in claim 11 wherein the contouring means is also in contact with said body.

14. A lens as in claim 11 wherein said recovery releases said haptic from a position close to the periphery of said body, said haptic moving away from the periphery of said body.

15. An intraocular lens comprising:
a lens body of generally soft material; and
contouring means of shape memory alloy operatively connected to said lens body to change the overall dimensions of the lens for inplantation of the lens wherein the shape memory alloy is pseudoelastic displaying reversible, stress-induced martensite at body temperature.

16. A lens as in claim 15 wherein said lens includes at least one haptic and said contouring means is in operative contact with said haptic to move said haptic.

17. An intraocular lens comprising:
a lens body of generally soft material; and
contouring means of shape memory alloy operatively connected to said lens body to change the overall dimensions of the lens for implantation of the lens wherein the shape memory alloy has a martensitic state and an austenitic state, said means capable of being deformed dimensionally while in the martensitic state, a change from the martensitic state to the austenitic state recovering said means to its nondeformed dimension to change the overall dimensions of the lens.

18. A lens as in claim 17 wherein said lens includes at least one haptic and said contouring means is in operative contact with said haptic to move said haptic.

19. An intraocular lens comprising:
a lens body of generally soft material;
at least one flexible haptic connected to said lens body; and
contouring means of shape memory alloy integral with a portion of said lens body and said haptic to change the overall dimensions of said lens wherein the shape memory alloy is pseudoelastic displaying reversible stress-induced martensite at body temperature.

20. An intraocular lens comprising:
a lens body of generally soft material;
at least one flexible haptic connected to said lens body; and
contouring means for shape memory alloy integral with a portion of said lens body and said haptic to change the overall dimensions of said lens wherein the shape memory alloy has a martensitic state and an austenitic state, said means capable of being deformed dimensionally while in the martensitic state, a change from the martensitic state to the austenitic state recovering said means to its nondeformed dimensions to change the overall dimensions of the lens.

21. A method of installing the intraocular lens of claims 15, 16, 17, 18, 19 or 20 comprising the steps of:

providing an intraocular lens having a lens body of generally soft material and a contouring means of shape memory alloy, said means capable of recoverable deformation, said means being operatively connected to said body to change the overall dimensions of the lens;

deforming said lens to a smaller overall dimension;

positioning said lens in the body; and recovering said means to a large overall dimension.

* * * * *

UNITED STATES PATENT AND TRADEMARK OFFICE
CERTIFICATE OF CORRECTION

PATENT NO. : 4,666,445
DATED : May 19, 1987
INVENTOR(S) : Michael J. Tillay

It is certified that error appears in the above-identified patent and that said Letters Patent is hereby corrected as shown below:

Column 3, line 52, "allays" should be --alloys--.

Column 7, line 8, "alloY" should be --alloy--.

Column 10, line 22, "forcefit" should be --force-fit--.

Column 13, line 65, "vetreous" should be --vitreous--.

Column 13, line 66, "post-perative" should be --post-operative--.

Column 15, line 16, "capable for" should be --capable of--.

Column 16, line 29, "inplantation" should be --implantation--.

Column 16, line 65, "means for" should be --means of--.

Signed and Sealed this

Sixth Day of September, 1988

Attest:

DONALD J. QUIGG

Attesting Officer

Commissioner of Patents and Trademarks